US006166248A

United States Patent [19]

Heida et al.

[11] Patent Number: 6,166,248

[45] Date of Patent: Dec. 26, 2000

[54] PROCESS FOR THE SEPARATION OF ACRYLIC ACID

[75] Inventors: Bernd Heida, Ellerstadt; Fritz Thiessen, Ludwigshafen; Ulrich Hammon, Mannheim; Albrecht Dams, Wachenheim, all of Germany

[73] Assignee: BASF Aktiengesellschaft, Ludwigshafen, Germany

[21] Appl. No.: 09/147,628

[22] PCT Filed: Aug. 1, 1997

[86] PCT No.: PCT/EP97/04214

§ 371 Date: Feb. 4, 1999

§ 102(e) Date: Feb. 4, 1999

[87] PCT Pub. No.: WO98/05622

PCT Pub. Date: Feb. 12, 1998

[30] Foreign Application Priority Data

Aug. 5, 1996 [DE] Germany ........................... 196 31 645

[51] Int. Cl.[7] .......................... C07C 51/16; C07C 241/00

[52] U.S. Cl. ............................................ 562/545; 562/600

[58] Field of Search ..................................... 562/545, 600

[56] References Cited

U.S. PATENT DOCUMENTS 3,932,500 1/1976 Duembgen et al. .
4,110,370 8/1978 Engelbach et al. .
5,426,221 6/1995 Willersinn .

FOREIGN PATENT DOCUMENTS 21 36 396 2/1973 Germany .
24 49 780 4/1976 Germany .
43 08 087 9/1994 Germany .

OTHER PUBLICATIONS

I.M. Korenman, et al., Zhurnal Prikladnoi Khimii, vol. 45, No. 5, "Distribution of Acrylic Acid Between Organic Solvents and Water", May 1972, English Translation Only, pps. 1101–1105, (translated from the original transcript of pps. 1078–1082).

*Primary Examiner*—Paul J. Killos
*Attorney, Agent, or Firm*—Oblon, Spivak, McClelland, Maier & Neustadt, P.C.

[57] ABSTRACT

A process for isolating acrylic acid forward during catalytic gas phase oxidation of propene, which entails separating acrylic acid from the gas phase oxidation reaction using an absorbent containing biphenyl, diphenyl ether or dimethyl phthalate; and extracting acrylic acid from acid water of the gas phase reaction with a solvent containing biphenyl, diphenyl ether or dimethyl phthalate.

8 Claims, 1 Drawing Sheet

PROCESS FOR THE SEPARATION OF ACRYLIC ACID

BACKGROUND OF THE INVENTION

1. Field of the Invention

The present invention relates to a process for preparing acrylic acid by catalytic gas phase oxidation, in particular to recovery of acrylic acid from the acid water produced.

2. Description of the Background

Acrylic acid can be prepared from propene by catalytic gas phase oxidation. The propene to be oxidized can be mixed with a diluent gas or with a circulated gas containing unreacted starting materials. The gas-phase oxidation reaction mixture is passed to an absorption column to separate off the acrylic acid. There, the acrylic acid is substantially separated off from the mixture of reaction products using solvents such as lactams, for example methylpyrrolidone, or other organic acids, for example ethylhexanoic acid. The non-absorbed components are taken off from the absorption column in the gaseous state and fed to a condensation stage. The condensible and condensed part of this gas mixture is separated off and led off as what is termed acid water. The uncondensible gaseous part, in contrast, is in part recycled to the gas phase oxidation and forms the circulated gas. The acid water is generally incinerated. Thus, although many low- and medium-boilers are removed from the production cycle, acrylic acid present in the acid water is also destroyed.

This loss of acrylic acid can be avoided by distilling the acid water or extracting it with suitable compounds. Suitable compounds for extracting acrylic acid from aqueous solutions are specified by I. M. Korenman et al. in "Distribution of acrylic acid between organic solvents and water" (translation by Consultants Bureau, New York, from Zhurnal Prikladnoi Khimii, Vol. 45, No. 5, May 1972, pp. 1078–1082), including dimethyl phthalate. Distillation has the disadvantage of a high energy consumption, and extraction leads to a not inconsiderable additional use of equipment, since, in addition to extracting the acid water, it is necessary to distil or strip the solvent from the extract phase. This cycle for recovering acrylic acid from the acid water is complicated, especially, by the need to avoid as far as possible carrying over the solvent used there into the preparation cycle, since the presence of further organic solvents in the preparation cycle can adversely effect the quantitative yield and the quality of the acrylic acid present. It is highly complicated to exclude adverse effects of this type reliably.

SUMMARY OF THE INVENTION

It is an object of the present invention therefore to find an efficient process for preparing acrylic acid in which acrylic acid can be additionally recovered from the acid water in a simple and effective manner.

DETAILED DESCRIPTION OF THE PREFERRED EMBODIMENTS

Figure 1:
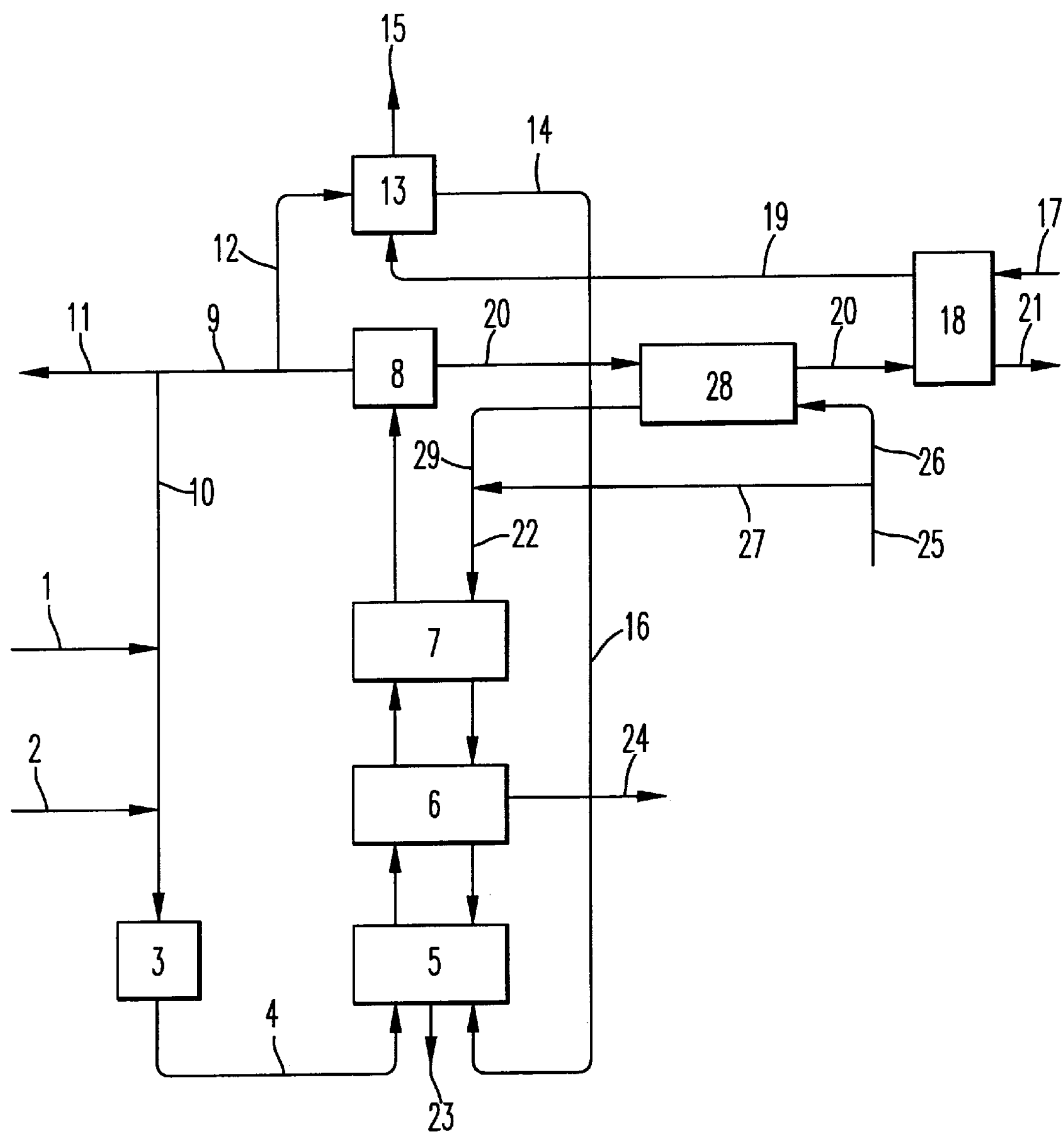

We have found that this object is achieved by the process for preparing acrylic acid by catalytic gas phase oxidation of propene, acrylic acid being absorbed from the gas phase oxidation reaction mixture in an absorption stage using a first solvent, a gas mixture being taken off from the absorption stage which is low in the first solvent and in acrylic acid, the gas mixture being cooled in a condensation stage, preferably to a temperature of from 20° C. to 60° C., the condensed phase of the gas mixture from the condensation stage being taken off as acid water and the gaseous phase of the gas mixture being taken off from the condensation stage and at least in part recycled as circulated gas to the gas phase oxidation. In the process of the invention the first solvent comprises at least one substituted or unsubstituted biphenyl, a substituted or unsubstituted diphenyl ether or dimethyl phthalate, and acrylic acid is extracted from the acid water in an acid water-extraction stage using a second solvent which comprises at least one substituted or unsubstituted biphenyl, a substituted or unsubstituted diphenyl ether or dimethyl phthalate.

Preferably, the first solvent used is a mixture which comprises biphenyl and diphenyl ether and/or dimethyl phthalate, in particular a mixture which comprises from 60 to 100, preferably 70 to 90, % by weight of substituted or unsubstituted biphenyl and substituted or unsubstituted diphenyl ether and from 0 to 40, preferably from 10 to 30, % by weight of dimethyl phthalate. Particularly preferably, both the biphenyl and also the diphenyl ether are unsubstituted. The weight ratio of diphenyl ether to biphenyl is preferably from 4:1 to 2:1. A particularly preferred solvent is a mixture which comprises from 40 to 80% by weight of unsubstituted diphenyl ether, from 10 to 30% by weight unsubstituted biphenyl and from 10 to 30% by weight of dimethyl phthalate. Furthermore, the solvent can comprise further constituents, for example to increase the selectivity of the extraction medium used.

A gas mixture which is low in the first solvent and acrylic acid is taken off from the absorption stage. The concentration of acrylic acid in the gas mixture is typically below 1% by weight, preferably below 0.5% by weight. This gas mixture is cooled in a condensation stage, preferably to from 20° C. to 60° C. The condensed phase of the gas mixture is taken off from the condensation stage as acid water, and the gaseous phase of the gas mixture is taken off from the condensation stage and at least in part recycled as circulated gas to the gas phase oxidation. According to the present invention, acrylic acid is then extracted from the acid water in an acid water extraction stage using a second solvent which comprises at least one substituted or unsubstituted biphenyl, a substituted or unsubstituted diphenyl ether or dimethyl phthalate. The second solvent preferably comprises at least 40, particularly preferably at least 70, % by weight of dimethyl phthalate. The process of invention offers the advantage that, with efficient extraction of the acrylic acid from the acid water, there is no need to ascertain whether the second solvent is carried over into the preparation cycle, since components are used both in the first and second solvent which have no adverse effect on product quality or yield. A limited carryover may even be desirable and may be used to have a specific effect on the composition of the first solvent which changes during the process.

Preferably, the acid water, upstream of the acid water extraction stage, is fed to a preextraction stage in which medium-boilers, for example maleic anhydride, are extracted from the first solvent using acid water as extraction medium. Regularly, only a part-stream of the first solvent is fed to this preextraction of medium-boilers. The acrylic acid concentration in the acid water can decrease slightly owing to this extraction. The extract, i.e. the aqueous phase, of the preextraction stage is then according to the invention fed to the acid water extraction stage.

Further preference is given to a variant of the process of the invention in which acrylic acid is desorbed from the extract phase of the acid water extraction stage using circulating gas or portions of the circulated gas, that is part-streams of identical or different composition as the overall circulated gas, or using constituents of circulated gas, for example nitrogen or oxides of carbon. However, nitrogen or air can alternatively be used as desorbents. The preferred use of circulated gas has the advantage that no addition desorbent need be provided or tested for compatibility with the other components in the circuit. Compared with distillation, desorption, furthermore, has the fundamental advantage that neither an evaporator nor a condenser need be provided, which considerably decreases the constructional expenditure of an acrylic acid production plant.

The present invention is described in detail below with reference to FIG. 1, a block diagram of a process according to the invention for preparing acrylic acid.

Propene via line 1, a diluent gas (circulated gas or steam), for example air or steam, via line 10 and air via line 2 are fed to a reactor 3 in which the catalytic gas phase oxidation of propene proceeds. The acrolein formed in the reaction can be oxidized in a further reactor which is not shown. The gas phase oxidation reaction mixture passes via line 4 to quenching apparatus 5. There, the reaction mixture is cooled and a part of the absorbent (solvent) is evaporated which is fed via line 22 to the absorption column 7 and is passed from there via a cooling unit 6 to the quenching apparatus 5. High-boiling minor components of the solvent are condensed in the quenching apparatus 5 and taken off via a withdrawal line 23. They are disposed of, for example by being incinerated, with or without distilling off solvent in advance. The previously intensively cooled reaction mixture is passed from the quenching apparatus 5 onto the cooling unit 6, which, for example, comprises cooling circuits, where the reaction mixture is cooled to the appropriate absorption temperature. The reaction mixture is then passed into the absorption column 7. There, acrylic acid is separated off from the gas phase oxidation reaction product by countercurrent absorption using the solvent fed via line 22. This solvent can comprise, for example, a mixture of about 60% by weight of unsubstituted diphenyl ether, 20% by weight of unsubstituted biphenyl and 20% by weight of dimethyl phthalate. It can, furthermore, also have further polar solvents for reducing the production of solids or else components to increase selectivity. The solvent laden with acrylic acid is passed to cooling unit 6 and withdrawn from this via side takeoff 24 for further workup not shown here.

This workup generally comprises stripping of low boilers and, if necessary, solvent distillation or an equivalent step.

The reaction products substantially freed of acrylic acid are taken off overhead from the absorption column 7 and passed to the quenching apparatus 8. There, the uncondensible part is taken off via line 9 and, after separating off and leading off inert gas components via line 11, is recycled as circulated gas via line 10 to the gas phase oxidation of propene. This circulated gas comprises, inter alia, unreacted starting materials of the gas phase oxidation, nitrogen and oxides of carbon. The condensible part of the reaction products freed of acrylic acid is taken off via line 20. This condensate which is termed acid water consists of an aqueous solution which, in addition to acrylic acid, further comprises relevant amounts of acetic acid, maleic acid and formaldehyde, as well as other acids.

In accordance with the present invention, the acid water is passed to an extraction stage 18 via line 20 to recover a considerable proportion of the acrylic acid still present therein. There, the second solvent fed via line 17 takes up the acrylic acid. This extraction medium can, for example, consist of dimethyl phthalate or comprise substantial amounts thereof. The acrylic-acid-laden extraction medium is passed via line 19 to the stripping column 13, where circulated gas fed via line 12 separates the acrylic acid from the extraction medium. The acrylic-acid-laden extract can then be recycled via line 14 to the quenching apparatus 5. However, the recycling can also be accomplished at any other suitable point in the process. The extraction medium is conducted away from the stripping column 13 via line 15 and can be reused as solvent by feeding it back in line 17.

Upstream of the acid water extraction in extraction stage 18, the acid water from quenching apparatus 8 is preferably, as shown, fed to an acid water preextraction stage 28 arranged in line 20. In the preextraction stage 28, medium-boilers, in particular maleic acid, are extracted from the first solvent using the acid water from a part-stream 26 of the first solvent which is introduced via line 25 and is recycled from the solvent distillation or other workup steps. The part-stream 26 typically comprises about 10% of the volume of the main stream 25 of the solvent. The part-stream 29 of the first solvent which is depleted in medium-boilers is then, together with its main stream 27, passed via line 22 to the absorption column 7. The acid water is passed via the second part of line 20 to the extraction stage 18.

The process of the invention thus offers, with minimum expenditure on equipment and without using substances external to the process, a higher yield of acrylic acid, because the losses of acrylic acid via the acid water can be virtually completely eliminated.

We claim:

1. A process for isolating acrylic acid formed during catalytic gas phase oxidation of propene, which comprises:

a) absorbing acrylic acid from the gas phase oxidation reaction mixture in an absorption stage using a first solvent, which solvent comprises at least one substituted or unsubstituted biphenyl, a substituted or unsubstituted diphenyl ether or dimethyl phthalate, b) removing a gas mixture in a condensation stage, c) cooling the gas mixture in a condensation stage, d) removing the condensed phase of the gas mixture from the condensation stage as acid water, e) removing the gaseous phase of the gas mixture from the condensation stage and recycling a least a portion thereof as circulated gas to the gas phase oxidation, wherein acrylic acid is extracted from the acid water in an acid water extraction stage using a second solvent which comprises at least one substituted or unsubstituted biphenyl, a substituted or unsubstituted diphenyl ether or dimethyl phthalate;

f) desorbing the acrylic acid from the extract phase of the acid water extraction stage using air, nitrogen, or circulated gas;

g) recycling the desorbed extracted acrylic acid from f) to step a).

2. The process as claimed in claim 1, wherein the first solvent comprises substituted or unsubstituted biphenyl and substituted or unsubstituted diphenyl ether or dimethyl phthalate or a mixture thereof.

3. The process as claimed in claim 1, wherein said first solvent comprises a mixture of:

i) from 60 to 100% by weight of substituted or unsubstituted biphenyl and substituted or unsubstituted diphenyl ether, and ii) from 0 to 40% by weight of dimethyl phthalate.

4. The process as claimed in claim 3, wherein in said solvent mixture, component i) is present in an amount from 70 to 90% by weight; and component ii) is present in an amount of from 10 to 30% by weight.

5. The process as claimed in claim 3, wherein said first solvent comprises a mixture of:

i) from 40 to 80% by weight of unsubstituted diphenyl ether, ii) from 10 to 30% by weight of unsubstituted biphenyl, and iii) from 10 to 30% by weight of dimethyl phthalate.

6. The process as claimed in claim 3, wherein the second solvent comprises at least 40% by weight of dimethyl phthalate.

7. The process as claimed in claim 6, wherein a second solvent comprises at least 70% by weight of dimethyl phthalate.

8. The process as claimed in claim 3, wherein the acid water, upstream of the acid water extraction stage, is fed to a preextraction stage in which medium-boilers, in particular maleic anhydride, are extracted from the first solvent using the acid water, and the extract of the preextraction stage is fed to the acid water extraction stage.

* * * * *